(12) United States Patent
Lee et al.

(10) Patent No.: US 7,579,151 B2
(45) Date of Patent: Aug. 25, 2009

(54) ISOLATION AND PURIFICATION METHOD OF BIOMOLECULES USING HYDROGEL

(75) Inventors: Young-sun Lee, Gyeonggi-do (KR); Jung-im Han, Seoul (KR); Hyo-yeon Lee, Gyeonggi-do (KR); Kak Namkoong, Seoul (KR); Kwang-wook Oh, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 227 days.

(21) Appl. No.: 11/191,221

(22) Filed: Jul. 27, 2005

(65) Prior Publication Data

US 2006/0127887 A1    Jun. 15, 2006

(30) Foreign Application Priority Data

Dec. 10, 2004    (KR) .................... 10-2004-0104025

(51) Int. Cl.
*C12Q 1/68*    (2006.01)
*C07H 21/00*    (2006.01)

(52) U.S. Cl. .......................................... 435/6; 536/25.4
(58) Field of Classification Search ...................... None
See application file for complete search history.

(56) References Cited

U.S. PATENT DOCUMENTS

| | | | | |
|---|---|---|---|---|
| 5,705,628 | A | 1/1998 | Hawkins ................ | 536/25.4 |
| 5,804,684 | A * | 9/1998 | Su .......................... | 536/25.4 |
| 6,258,996 | B1 * | 7/2001 | Goldman ................ | 604/368 |
| 2003/0008320 | A1 * | 1/2003 | Baker ..................... | 435/6 |
| 2003/0218130 | A1 * | 11/2003 | Boschetti et al. ....... | 250/288 |
| 2004/0157244 | A1 * | 8/2004 | Budahazi et al. ....... | 435/6 |
| 2006/0121116 | A1 * | 6/2006 | Mori et al. ............. | 424/486 |

FOREIGN PATENT DOCUMENTS

KR    2001-0101994    11/2001

OTHER PUBLICATIONS

Elaissari et al. Hydrophilic magnetic latex for nucleic acid extraction, purification and concentration. Journal of Magnetism and Magnetic Materials (2001) 225: 127-133.*
Dissing et al. Polyelectrolyte complexes as vehicles for affinity precipitation of proteins. Journal of Biotechnology (1996) 52: 1-10.*
Nakamae et al. Synthesis and characterization of stimuli-sensitive hydrogels having a different length of ethylene glycol chains carrying phosphate groups: loading and release of lysozyme. Journal of Biomaterials Science Polymer Edition (2004) 15(11): 1435-1446.*
Jensen et al. Loading into and electro-stimulated release of peptides and proteins from chondroitin 4-sulphate hydrogels. European Journal of Pharmaceutical Sciences (2002) 15: 139-148.*
Olsen et al. Immobilization of DNA hydrogel plugs in microfluidic channels. Analytical Chemistry (2002) 74(6): 1436-1441.*
Tarcha et al. Absorption-enhanced solid-phase immunoassay method via water-swellable poly(acrylamide) microparticles. Journal of Immunological Methods (1989) 125: 243-249.*
Tabata et al. In vitro sorption and desorption of basic fibroblast growth factor biodegradable hydrogels. Biomaterials (1998) 19: 1781-1789.*
Kondo et al. Preparation of thermo-sensitive magnetic hydrogel microspheres and application to enzyme immobilization. Journal of Fermentation and Bioengineering (1997) 84(4): 337-341.*
Sato et al. Hydrogel-microsphere-enhanced surface plasmon resonance for the detection of a K-ras point mutation employing peptide nucleic acid. Journal of Biomaterials Science Polymer Edition (2003) 14(8): 803-820.*
An Office Action of Korean Intellectual Property Office, regarding corresponding patent applicaton No. 10-2004-0104025.
All the references cited in the Search Report are listed above.
"Rapid, Universal Method to Isolate PCR-Ready DNA Using Magnetic Beads"; Authors: K. Rudi, et al.; BioTechniques vol. 22, No. 3, pp. 506-511 (1997).
"Rapid Isolation of PCR-Ready DNA From Blood, Bone Marrow and Cultured Cells, Based on Paramagnetic Beads"; Authors: Arne Deggerdal and Frank Larsen.

* cited by examiner

*Primary Examiner*—Kenneth R. Horlick
*Assistant Examiner*—Angela Bertagna
(74) *Attorney, Agent, or Firm*—Cantor Colburn, LLP

(57) ABSTRACT

Provided is a method of isolating and purifying biomolecules using a hydrogel, the method including: bring a sample containing charged biomolecules into contact with a hydrogel to bind the biomolecules to the hydrogel; washing the hydrogel bound with the biomolecules; and eluting the bound biomolecules using an elution solvent. According to the method, the use of a hydrogel with a large surface area reduces the isolation time of biomolecules to 5 min or less, an external device such as an electromagnet is not required, and small-sized systems or LOC can be easily implemented due to applicability to microsystems through a polymer patterning technique.

15 Claims, 10 Drawing Sheets

0 MIN         5 MIN         80 MIN

ANODE pH = 2.5  CATHODE pH = 13.5  CATHODE pH = 13.5
0 MIN          5 MIN                10 MIN

ISOLATION AND PURIFICATION METHOD OF BIOMOLECULES USING HYDROGEL

This application claims the benefit of Korean Patent Application No. 10-2004-0104025, filed on Dec. 10, 2004, in the Korean Intellectual Property Office, the disclosure of which is incorporated herein in its entirety by reference.

BACKGROUND OF THE INVENTION

1. Field of the Invention

The present invention relates to an isolation and purification method of biomolecules using a hydrogel.

2. Description of the Related Art

Isolation methods of DNA from cells were performed using materials that have the proclivity of binding to DNA. Examples of materials for isolation methods of DNA are silica, glass fiber, anion exchange resin and magnetic beads (Rudi, K. et al., *Biotechniqures* 22, 506-511 (1997); and Deggerdal, A. et al., *Biotechniqures* 22, 554-557 (199)). To avoid the manual steps and remove operator error, several automatic machines were developed for high-throughput DNA extraction.

Conventionally, a method of purifying nucleic acids using a solid phase was known. For example, U.S. Pat. No. 5,234,809 discloses a method of purifying nucleic acids using a solid phase to which nucleic acids are bound. However, this method is time consuming and complicated, and thus is not suitable for a Lab-On-a-Chip (LOC). The method also has a problem in the use of a chaotropic material. That is, when the chaotropic material is not used, nucleic acids are not bound to the solid phase.

U.S. Pat. No. 6,291,166 discloses a method of archiving nucleic acids using a solid phase matrix. This method is advantageous in that since nucleic acids are irreversibly bound to the solid phase matrix, a delayed analysis or repeated analysis for the nucleic acid solid phase matrix complexes is possible. However, according to this method, aluminum (Al) which has a positively-charged surface should be rendered hydrophilic with basic materials, such as NaOH, and nucleic acids are irreversibly bound to the Al rendered hydrophilic, and thus cannot be separated from Al.

U.S. Patent Publication No. 2001/18513 discloses a method for extracting biomolecules from a biological sample, the method including: at a first pH, bringing the biological sample into contact with a solid phase such that the biomolecules are bound to the solid phase; and extracting the biomolecules bound to the solid phase using an elution solvent at a second pH. This method is a DNA isolation method using a material with the charge varied according to the pH and does not include the isolation of biomolecules using a hydrogel.

U.S. Pat. No. 5,705,628 discloses a method of reversibly and non-specifically binding DNA to magnetic microparticles having a carboxyl group-coated surface, the method including: combining magnetic microparticles having a carboxyl group-coated surface to a solution containing DNA; and adding the salt and polyethylene glycol onto the surfaces of the magnetic microparticles. However, in the method, the magnetic particles having a carboxylic group-coated surface, the salt and polyethylene glycol are used to isolate DNA, but the isolation of biomolecules using a hydrogel is not included.

Conventional isolation and purification methods of biomolecules requires external devices, such as an electromagnet, and had a problem of practicing time of at least about 30 min. Thus, a method of efficiently isolating and purifying biomolecules within 5 min without an external device is required.

Thus, the present inventors discovered that when biomolecules were isolated using a hydrogel which is ionized in a solution to have a varying surface, the isolation time can be shortened and an external device is not required, and thus this method can be easily applied to Microsystems.

SUMMARY OF THE INVENTION

The present invention provides a method of isolating and purifying biomolecules using a hydrogel, which can shorten the isolation time of biomolecules and does not require an external device.

According to an aspect of the present invention, there is provided a method of isolating and purifying biomolecules using a hydrogel, the method including: bring a sample containing charged biomolecules into contact with a hydrogel to bind the biomolecules to the hydrogel; washing the hydrogel bound with the biomolecules; and eluting the bound biomolecules using an elution solvent.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

A method according to the present invention includes bring a sample containing biomolecules into contact with a hydrogel to bind the biomolecules to the hydrogel. The hydrogel has a large surface area and is swollen and ionized by various stimuli such as pH, electricity, heat, ion, and the like. Thus, a hydrogel containing water is applicable to food additives, blood-contacting materials, bioadhesive, contact lens, wound dressing, artificial organs, drug-delivery systems, DNA vaccine, controlled-releasing preparations, membranes, super-absorbents, cell capsulating and immunoisolating materials, and bioactivator delivery carriers containing a drug.

Figure 1:
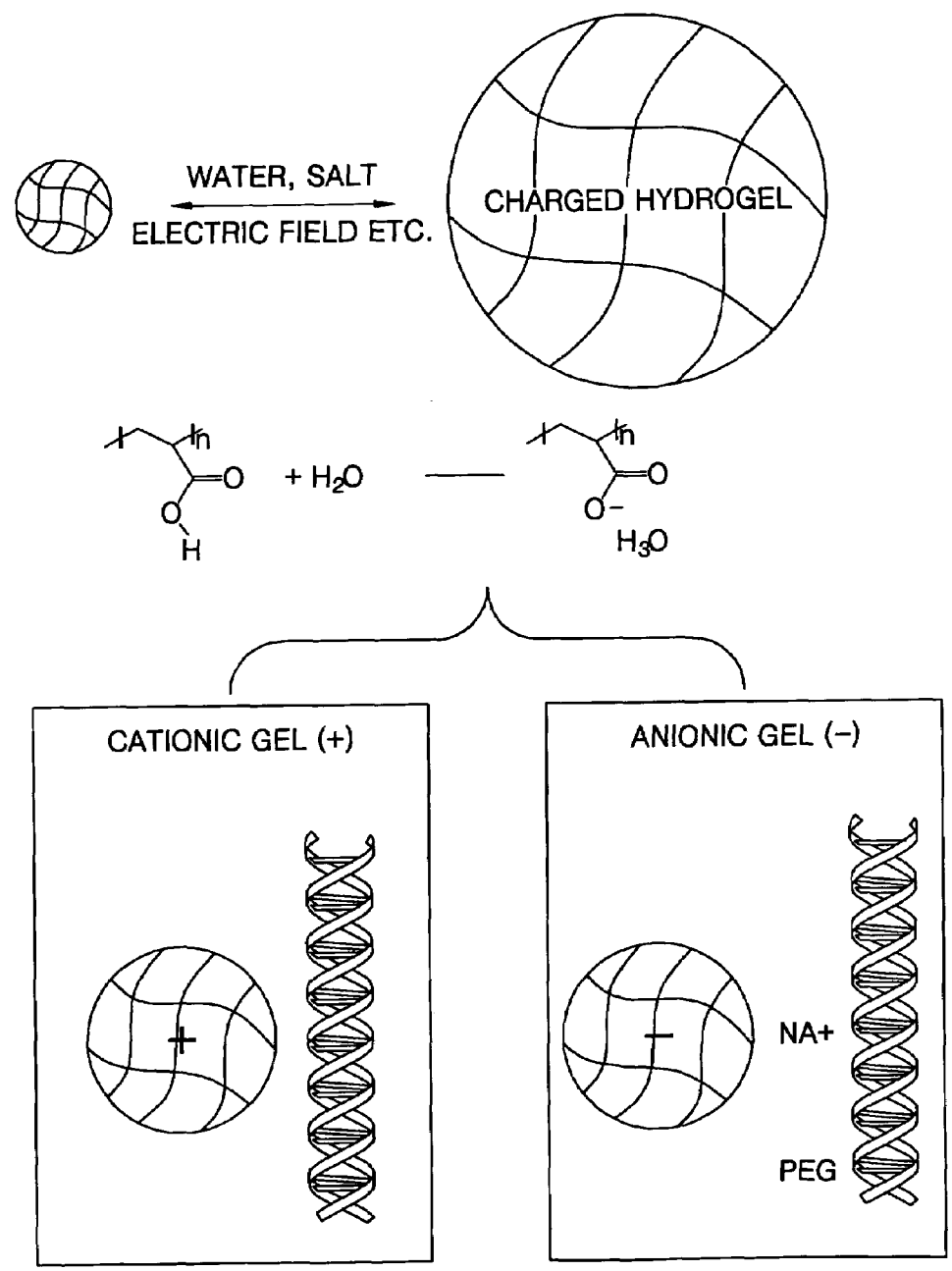
FIG. 1 is a schematic diagram illustrating embodiments that a hydrogel is swollen by water or an electric field and a charged hydrogel is bound to a nucleic acid.

The swelling of a hydrogel may be carried out by water or electrolysis. The hydrogel may be divided into an anionic hydrogel and a cationic hydrogel. Examples of a monomer of the anionic hydrogel include acrylic acid, methacrylic acid, vinylsulfonic acid, vinylphosphonic acid, maleic acid (including its anhydride), fumaric acid, itaconic acid, 2-acrylamido-2-methylpropanesulfonic acid, 2-acrylamido-2-methylpropanephosphonic acid, and the like. Examples of a monomer of the cationic hydrogel include N,N-ethylaminoethyl methacrylate, dimethyl aminopropyl methacrylamide, acrylamide, and the like. While the anionic hydrogel, such as polyacrylic acid, is more easily swollen and ionized with a higher pH, lower concentration of salt and lower temperature, the cationic hydrogel, such as poly(N,N-ethylaminoethyl methacrylate), is more easily swollen and ionized with lower pH and higher concentration of salt. FIG. 1 schematically illustrates embodiments that a hydrogel is swollen by water or an electric field and a charged hydrogel is bound to a nucleic acid. When a sample containing biomolecules is brought into contact with a swollen hydrogel, the biomolecules in the sample are bound to the hydrogel. The cationic hydrogel directly combines with negatively-charged biomolecules by electrostatic attraction forces and the anionic hydrogel combines with negatively-charged biomolecules by means of a mediator of polyethyle glycol/salt.

The method of the present invention also includes washing the hydrogel bound with the biomolecules. The washing step is for removing materials which are bound to the hydrogel. Organic solvents, such as 70% ethanol, may be used as a washing solvent and the washing conditions may be varied according to the types of the hydrogel and biomolecule to be isolated.

The method of the present invention also includes eluting the bound biomolecules using an elution solvent. The hydrogel bound with the biomolecules is washed using the solvent described above and is air dried to remove the solvent, and then is eluted using an elution solvent. The elution solvent may include water, Tris-HCl/pH 8, and Tris-HCl/pH 10. Among these solvents, water is preferable since it elutes more biomolecules than other solvents.

In an embodiment of the present invention, the hydrogel is an anionic hydrogel and a salt and polyethylene glycol may be further added in the binding of biomolecules and the hydrogel. While a cationic hydrogel can alone combine with negatively-charged biomolecules, an anionic hydrogel cannot alone combine with negatively-charged biomolecules and combines by means of a mediator of polyethylene glycol/salt. This is because the anionic hydrogel is negatively-charged and thus cannot combine with the negatively-charged biomolecules due to repulsive forces. Thus, the polyethylene glycol/salt acts as a material capable of neutralizing the repulsive forces. While polyprolylene glycol may be used in addition to polyethylene glycol, polyethylene glycol is generally used.

In an embodiment of the present invention, the anionic hydrogel may be polyacrylic acid. Examples of a monomer of the anionic hydrogel include polymerizable acids, such as acrylic acid, methacrylic acid, vinylsulfonic acid, vinylphosphonic acid, maleic acid and its anhydride, fumaric acid, itaconic acid, 2-acrylamido-2-methylpropanesulfonic acid and 2-acrylamido-2-methylpropanephosphonic acid, and salts thereof, for examples, sodium, potassium and ammonium salts, amides thereof, hydroxyalkyl esters, and amino or ammonium functional esters and amides.

Examples of the salt suitable to bind biomolecules to a hydrogel include halides of alkaline metal or alkaline earth metals, such as sodium chloride, lithium chloride, potassium chloride, calcium chloride, barium chloride, magnesium chloride and cesium chloride, but are not limited thereto. Sodium chloride may be generally used. The concentration of the salt is preferably 0.5 to 5.0 M. When the concentration of the salt is less than 0.5 M or exceeds 5.0 M, the number of biomolecules bound to the hydrogel is reduced. More preferably, the concentration of the salt is adjusted to be about 1.25 M.

The molecular weight of the polyethylene glycol is preferably 6,000 to 10,000. When the molecular weight of the polyethylene glycol is less than 6,000 or exceeds 10,000, the binding time between biomolecules and the hydrogel increases. More preferably, the molecular weight of the polyethylene glycol is about 8,000.

The concentration of the polyethylene glycol is preferably 5% to 15%. When the concentration of the polyethylene glycol is less than 5% or exceeds 15%, the yield of the bound biomolecules is reduced. More preferably, the concentration of the polyethylene glycol is about 10%.

In an embodiment of the present invention, the biomolecules may include prokaryotic cells, eukaryotic cells, viruses, nucleic acids, and the like. The biomolecules are not particularly restricted as long as they have a charged surface. Preferably, the biomolecule is a nucleic acid.

In an embodiment of the present invention, each of the binding time between biomolecules and the hydrogel and the elution time of biomolecules may be 0.5 to 1 min. When the binding time and the elution time are out of the above range, the recovery yield of biomolecules is reduced. More preferably, these times are about 1 min.

Figure 2:
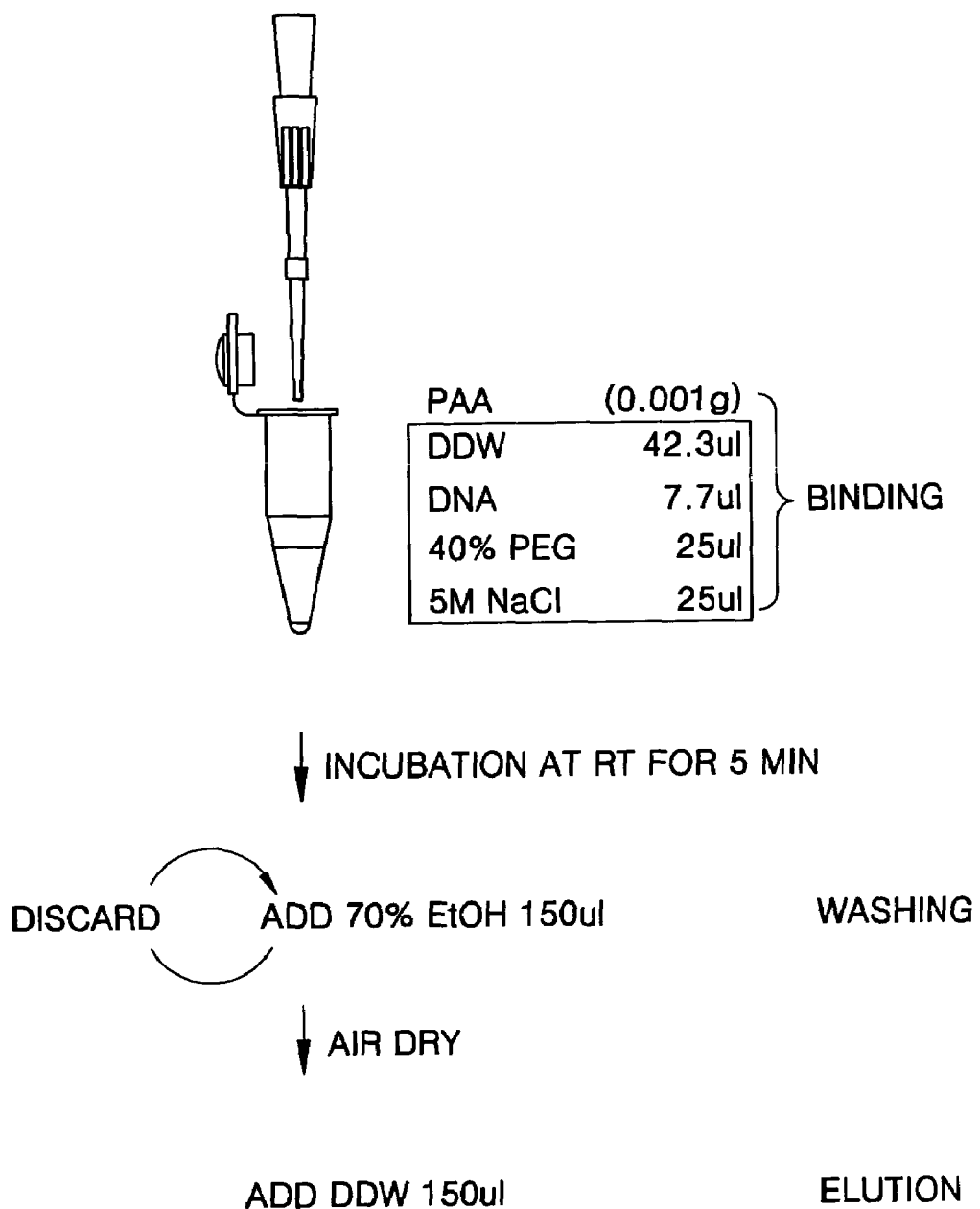
FIG. 2 is a flow chart illustrating an example of isolating nucleic acids using the method of the present invention.

FIG. 2 is a flow chart illustrating an example of isolating nucleic acids using the method of the present invention.

The present invention will now be described in greater detail with reference to is the following examples. The following examples are for illustrative purposes only and are not intended to limit the scope of the invention.

EXAMPLES

Example 1

Changes in Volume of Hydrogel by Solution or Electrolysis

Figure 3A:
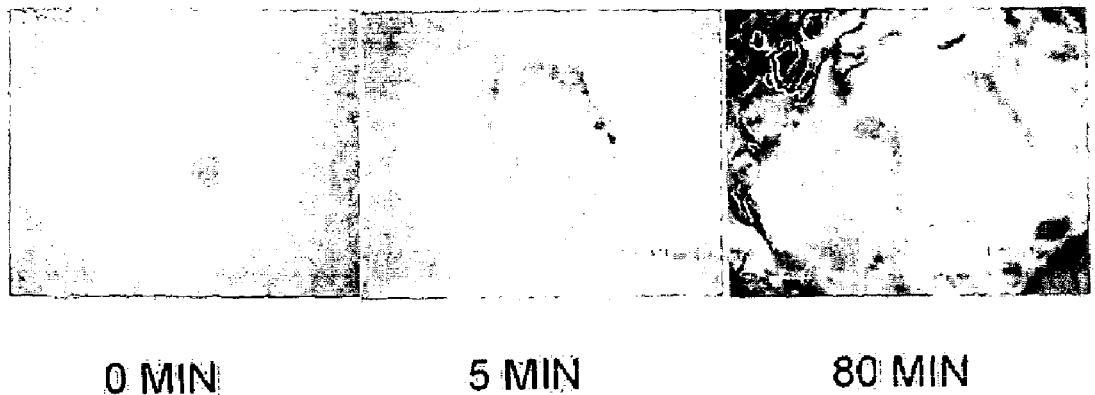
FIG. 3A shows microscopic photographs of polyacrylic acid (PAA) which has changes in volume by distilled water with respect to time and FIG. 3B is a graph illustrating changes in volume of the PAA by each of distilled water, 2.5 M NaCl (pH 8), and 0.5 M EDTA (pH 8) with respect to time.
Figure 3B:
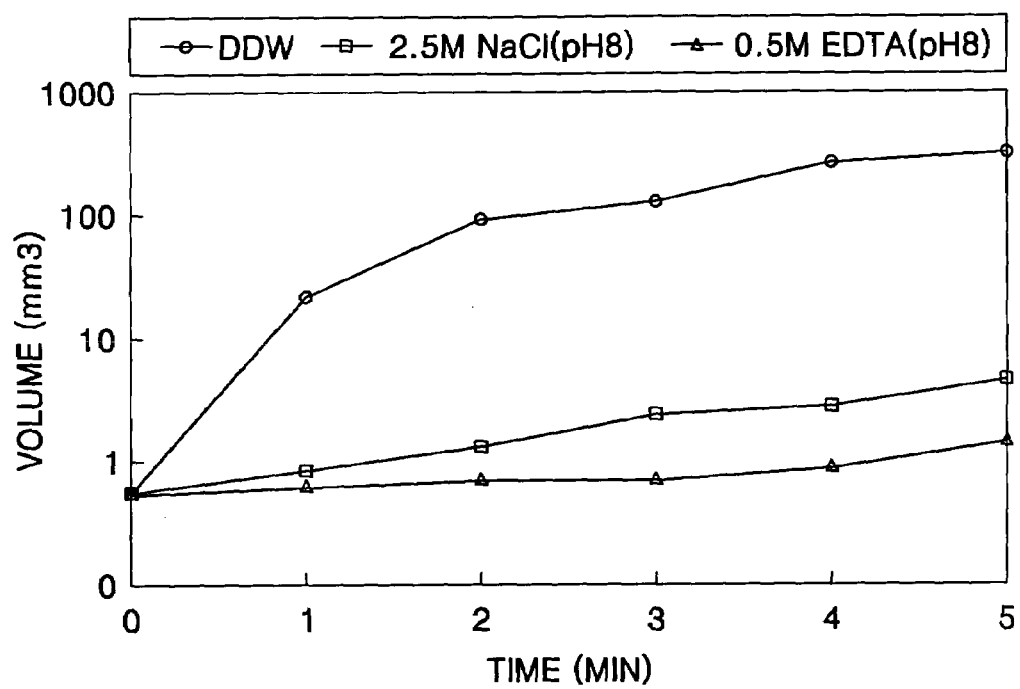

In this example, to observe the changes in volume of a hydrogel by a solution or electrolysis, polyacrylic acid (PAA) was used as the hydrogel. First, 0.001 g of the PAA was put into each of distilled water, 2.5 M NaCl (pH 8) and 0.5 M EDTA (pH 8) and the changes in volume of hydrogel by a solution with respect to time were observed. FIG. 3A shows microscopic photographs of the PAA in distilled water and FIG. 3B is a graph illustrating the changes in volume of the PAA by distilled water, 2.5 M NaCl (pH8) and 0.5M EDTA (pH8) with respect to time. Referring to FIG. 3B, the PAA in distilled water had the greatest increase in volume and became about 300 times larger than the initial volume after 5 min. Thus, it is assumed that the PAA swollen by distilled water can combine with more biomolecules.

Figure 4A:
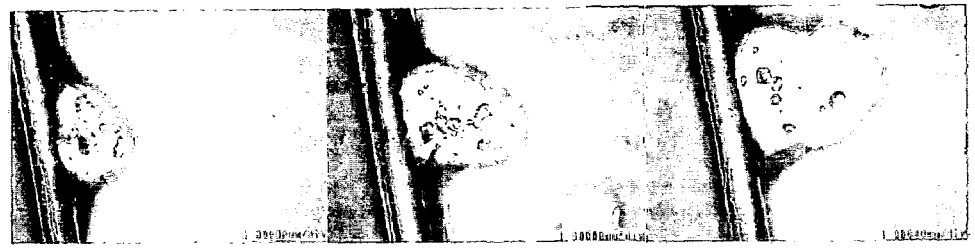
FIG. 4A shows microscopic photographs of the PAA which has changes in volume by electrolysis with respect to time and FIG. 4B is a graph illustrating changes in volume of the PAA by electrolysis with respect to time.
Figure 4B:
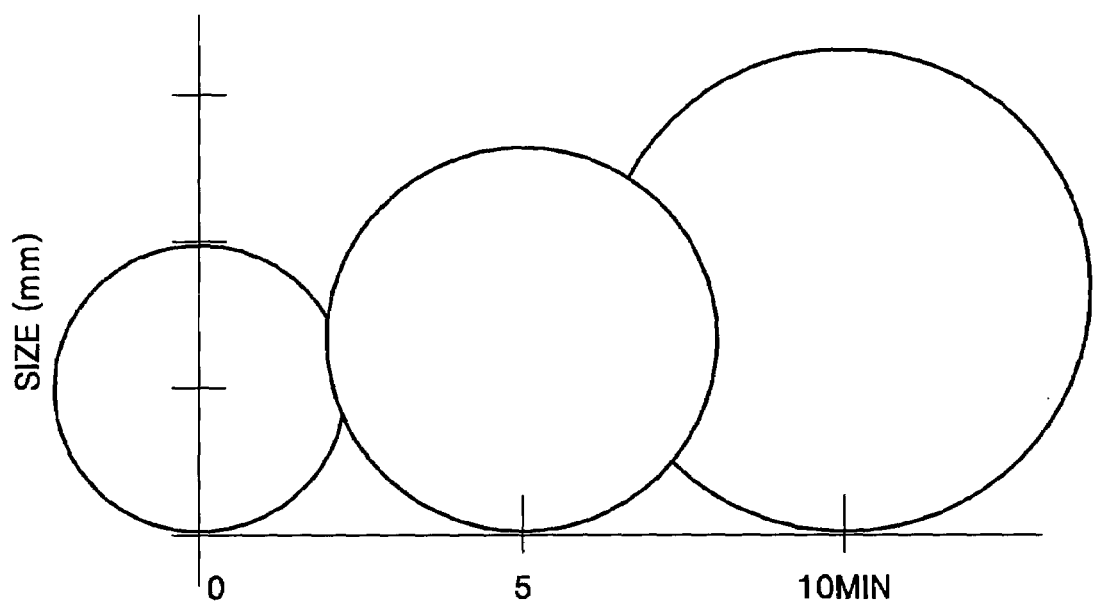

Electrolysis was also used to increase the volume of a hydrogel. Electrolysis was carried out in a 0.1 N NaCl solution at 5V and 0.01 A using 0.001 g of the PAA as the hydrogel. As a result, the PAA shrank at an anode (pH 2.5) and swelled at a cathode (pH 13.5). FIG. 4A shows microscopic photographs of the PAA under electrolysis and FIG. 4B illustrates changes in volume of the PAA with respect to time. Referring to FIG. 4B, the PAA became about 3 times larger than the initial volume after 5 min. Thus, while the PAA swollen by electrolysis has less of an increase in the volume than by water, it can also allow for more biomolecules to bind thereto.

Example 2

Isolation Efficiency of DNA According to Swelling Methods

To investigate the isolation efficiency of DNA according to swelling methods, 4 types of swelling methods were used. The first method included: mixing 0.001 g of the PAA with 42.3 µl of distilled water for 1 min; adding 7.7 µl (3 µg) of λ DNA and 25 µl of 5 M NaCl to the mixture; keeping the resultant at room temperature for 5 min to bind DNA to the PAA; washing the PAA having DNA bound thereto with 150 µl of 70% EtOH; drying the washed PAA in air for about 2-5 min; and eluting the bound DNA using 150 µl of distilled water. The second method included: mixing 0.001 g of the PAA with 42.3 µl of distilled water and 7.7 µl (3 µg) of λ DNA for 1 min; adding 25 µl of 5 M NaCl to the mixture; keeping the resultant at room temperature for 5 min to bind DNA to the PAA; washing the PAA having DNA bound thereto with 150 µl of 70% EtOH; drying the washed PAA in air for about 2-5 min; and eluting the bound DNA using 150 µl of distilled water. The third method was carried out in the same manner as the first method, except that in addition to 7.7 µl (3 µg) of λ DNA and 25 µl of 5 M NaCl, 25 µl of 40% PEG was further added to the mixture of the PAA and distilled water. The fourth method was carried out in the same manner as the second method, except that in addition to 25 µl of 5 M NaCl, 25 µl of 40% PEG was further added to the mixture of the PAA, distilled water and DNA.

Figure 5:
FIG. 5 illustrates the results of a 0.8% agarose gel electrophoresis of DNA eluted by 4 types of methods.

DNAs eluted by the above four methods were subjected to 0.8% agarose gel electrophoresis and the results are given in FIG. 5. Referring to FIG. 5, it can be seen that the third and fourth methods with PEG have higher DNA isolation efficiency than the first and second methods without PEG. Also, the fourth method in which PAA was swollen in the mixture of the PAA, distilled water and DNA have high DNA isolation efficiency than the third method in which PAA was swollen in the mixture of the PAA and distilled water. Thus, the fourth method, in which PAA was swollen in the mixture of the PAA, distilled water and DNA and both of PEG and NaCl were used, has the highest DNA isolation efficiency.

Example 3

Isolation Efficiency of DNA According to Binding Time

Figure 6:
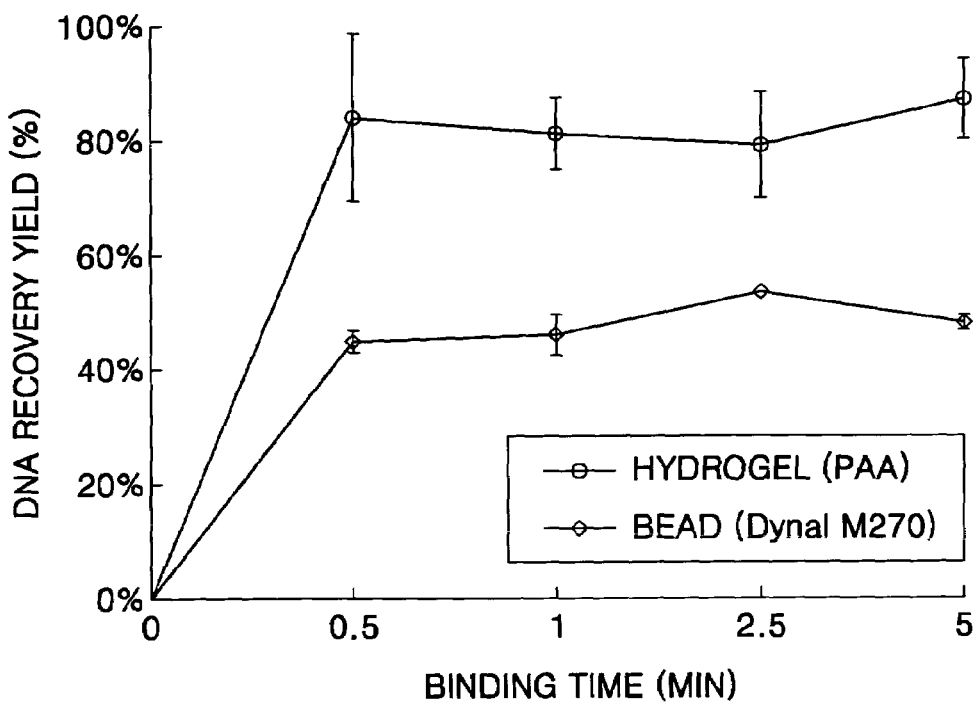
FIG. 6 is a graph illustrating the relationship between the recovery yield of DNA and the binding time.

To find out the isolation efficiency of DNA according to binding time of the PAA and DNA, the recovery yield of DNA with respect to time was investigated. The binding operation was carried out for 0.5, 1, 2.5 and 5 min and other procedures were the same as in the fourth method of Example 2. In addition, to compare the DNA isolation efficiency between the PAA and commercially available bead (Dynal M270) for isolating DNA, the above procedures were carried out, except that 0.001 g of the bead substituted for the PAA. FIG. 6 is a graph illustrating the relationship between the recovery yield of DNA and binding time. Referring to FIG. 6, it can be seen that the PAA has a much higher DNA recovery yield than the bead. In addition, the PAA has a DNA recovery yield of about 90%, even at the binding time of 30 sec. Thus, the method of the present invention can significantly reduce isolation time of DNA.

Example 4

Isolation Efficiency of DNA According to Concentration of DNA

Figure 7:
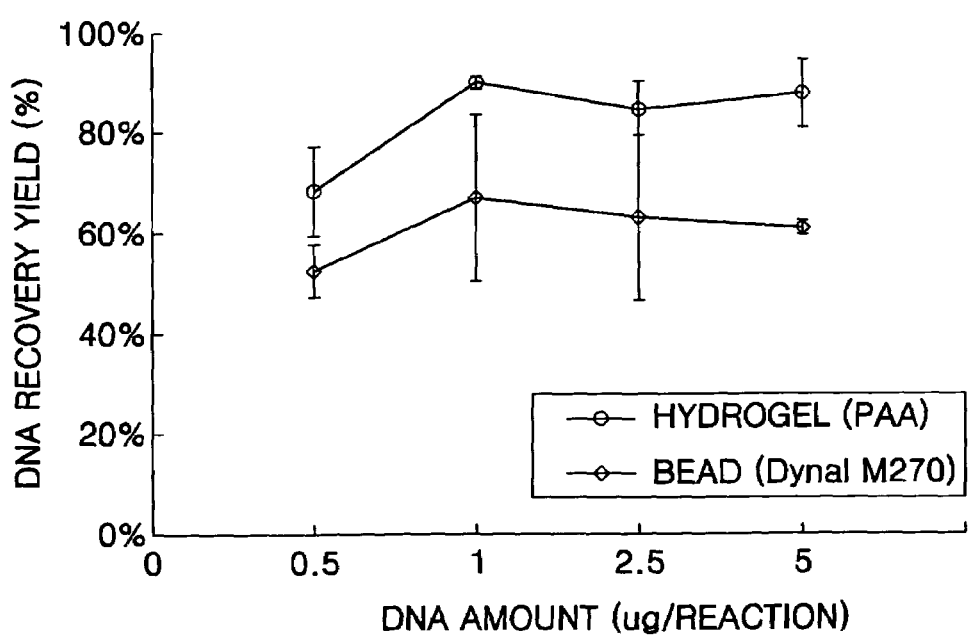
FIG. 7 is a graph illustrating the relationship between the recovery yield of DNA and the DNA concentration.

To find out the isolation efficiency of DNA according to the concentration of DNA, the recovery yield of DNA according to the concentration of DNA was investigated. The same procedures as in the fourth method of Example 2 were carried out, except that DNA was used in an amount of 0.1, 1, 2.5 and 5 µg per reaction and HBV plasmid DNA (7.5 kb) substituted for λ DNA. In addition, to compare the DNA isolation efficiency between the PAA and commercially available bead (Dynal M270) for isolating DNA, the above procedures were carried out, except that 0.001 g of the bead substituted for the PAA. FIG. 7 is a graph illustrating the relationship between the recovery yield of DNA and the concentration of DNA. Referring to FIG. 7, it can be seen that the PAA has a higher DNA recovery yield than the bead, which results from the PAA having a greater surface area than the bead. In addition, the recovery yield of DNA leads to about 90% at the concentration of DNA of 1 µg or more. Thus, the method of the present invention can efficiently isolate DNA, even at high concentrations of DNA.

Example 5

Isolation Efficiency of DNA According to Elution Solvent

Figure 8:
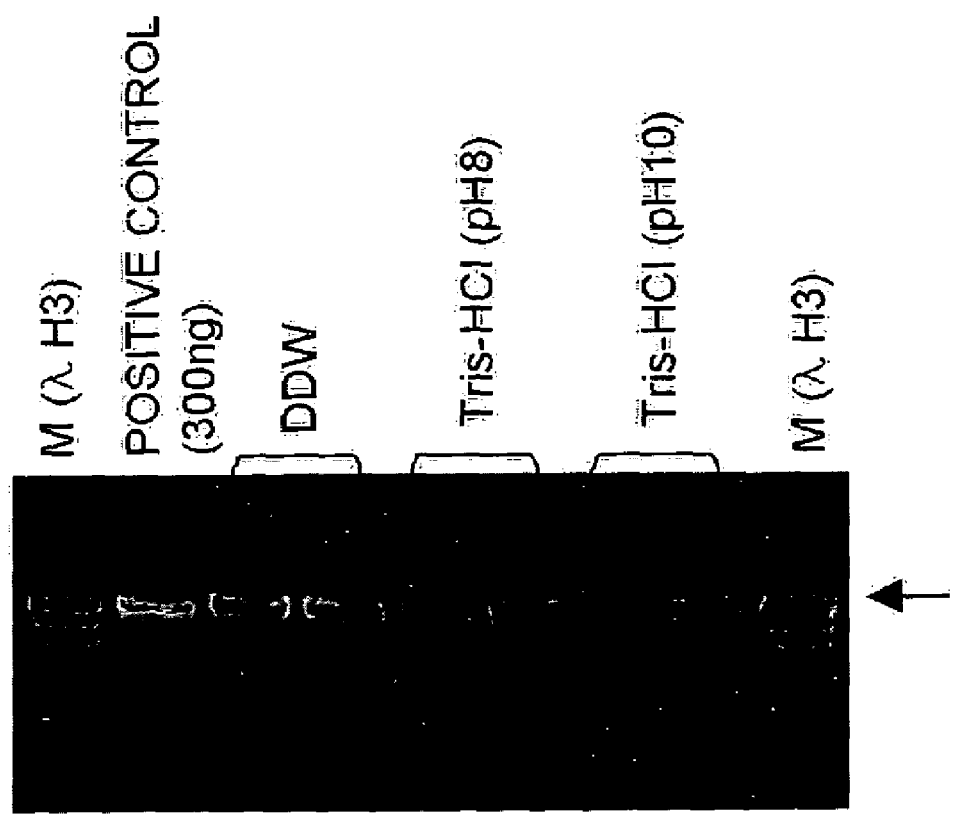
FIG. 8 shows the results of an agarose gel electrophoresis of DNA isolated by various elution solvents.

To find out the optimum conditions for elution, the isolation efficiency of DNA according to an elution solvent was investigated. The same procedures as in the fourth method of Example 2 were carried out, except that water, Tris-HCl (pH 8) and Tris-HCl (pH 10) were used as elution solvents. Samples of DNA isolated by the respective solvents were subjected to 0.8% agarose gel electrophoresis and the results are given in FIG. 8. In FIG. 8, the arrow denotes the position of a band of the isolated DNA. Referring to FIG. 8, it can be seen that water elutes the largest amount of DNA.

Example 6

Isolation Efficiency of DNA According to Elution Time

Figure 9:
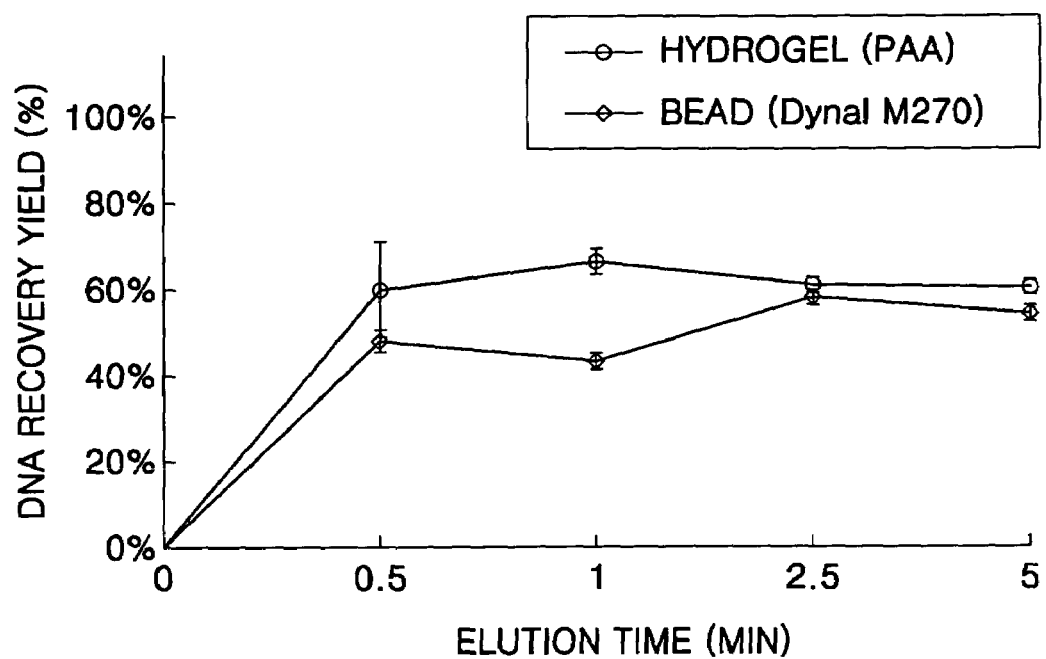
FIG. 9 is a graph illustrating the relationship between the recovery yield of DNA and the elution time.

To find out the isolation efficiency of DNA according to elution time, the recovery yield of DNA according to elution time was investigated. The same procedures as in the fourth method of Example 2 were carried out, except that the elution operation was performed for 0.5, 1, 2.5 and 5 min and HBV plasmid DNA (7.5 kb) substituted for λ DNA. In addition, to compare the DNA isolation efficiency between the PAA and commercially available bead (Dynal M270) for isolating DNA, the above procedures were carried out, except that 0.001 g of the bead substituted for the PAA. FIG. 9 is a graph illustrating the relationship between the recovery yield of DNA and the elution time. Referring to FIG. 9, it can be seen that the PAA had higher DNA recovery yield and reproducibility than the bead at all points of time. In addition, the DNA recovery yield of the PAA is very high even at elution time of 30 sec. Thus, the method of the present invention can significantly reduce DNA isolation time.

As described above, according to the present invention, the use of a large surface area of a hydrogel reduces the isolation time of biomolecules to 5 min or less, an external device such as an electromagnet is not required, and small-sized systems or LOC can be easily implemented due to applicability to microsystems through a polymer patterning technique.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of isolating and purifying nucleic acid using an anionic hydrogel, the method comprising:
    bringing a sample containing charged nucleic acid into contact with an anionic hydrogel to bind the nucleic acid to the anionic hydrogel,
    wherein the anionic hydrogel consists of a polymerizable acid or a polymerizable acid salt, and is swollen by water or electrolysis;
    washing the anionic hydrogel bound with the nucleic acid; and
    eluting the bound nucleic acid using an elution solvent,
    wherein the method is conducted in the absence of magnetic beads.

2. The method of claim 1, wherein in binding of the nucleic acid and the anionic hydrogel, a salt and polyethylene glycol are further added.

3. The method of claim 2, wherein the anionic hydrogel is polyacrylic acid.

4. The method of claim 2, wherein the polyethylene glycol has a molecular weight of 6,000 to 10,000 Da and the salt is a halide of alkaline metal or alkaline earth metal.

5. The method of claim 4, wherein the salt is selected from the group consisting of sodium chloride, lithium chloride, potassium chloride, calcium chloride, barium chloride, magnesium chloride and cesium chloride.

6. The method of claim 4, wherein the concentration of polyethylene glycol is 5 to 15% and the concentration of sodium chloride is 0.5 to 5.0 M.

7. The method of claim 6, wherein the concentration of sodium chloride is about 1.25M.

8. The method of claim 1, wherein each of binding time and elution time of the nucleic acid and hydrogel is 0.5 to 1 mm.

9. The method of claim 1, wherein the elution solvent is water.

10. The method of claim 5, wherein the concentration of polyethylene glycol is 5 to 15% and the concentration of sodium chloride is 0.5 to 5.0 M.

11. The method of claim 2, wherein each of binding time and elution time of the nucleic acid and anionic hydrogel is 0.5 to 1 mm.

12. The method of claim 2, wherein each of binding time and elution time of the nucleic acid and anionic hydrogel is 0.5 to 1 mm.

13. The method of claim 2, wherein the elution solvent is water.

14. The method of claim 3, wherein the elution solvent is water.

15. The method of claim 1, wherein the polymerizable acid or the polymerizable acid salt is selected from the group consisting of acrylic acid, methacrylic acid, vinylsulfonic acid, vinylphosphonic acid, maleic acid, maleic anhydride, fumaric acid, itaconic acid, 2-acrylamido-2-methylpropanesulfonic acid, and 2-acrylamido-2-methylpropanephosphonic acid.

* * * * *